(12) United States Patent
Rao

(10) Patent No.: US 8,372,580 B2
(45) Date of Patent: Feb. 12, 2013

(54) BRCA1 FUNCTION-BASED CELLULAR ASSAYS

(75) Inventor: Veena Rao, Atlanta, GA (US)

(73) Assignee: Morehouse School of Medicine, Atlanta, GA (US)

(\*) Notice: Subject to any disclaimer, the term of this patent is extended or adjusted under 35 U.S.C. 154(b) by 269 days.

(21) Appl. No.: 12/591,495

(22) Filed: Nov. 20, 2009

(65) Prior Publication Data
US 2011/0027814 A1 Feb. 3, 2011

Related U.S. Application Data

(60) Provisional application No. 61/193,371, filed on Nov. 21, 2008.

(51) Int. Cl.
*C12Q 1/00* (2006.01)
*C12Q 1/66* (2006.01)

(52) U.S. Cl. .............................. 435/4; 435/8

(58) Field of Classification Search .................. None
See application file for complete search history.

(56) References Cited

U.S. PATENT DOCUMENTS

| 5,747,282 | A | 5/1998 | Skolnick et al. |
| 5,750,400 | A | 5/1998 | Murphy et al. |
| 5,756,294 | A | 5/1998 | White et al. |
| 7,172,865 | B2 | 2/2007 | Heyduk |
| 7,507,800 | B2 | 3/2009 | Van Ommen et al. |

OTHER PUBLICATIONS

Aiyar et al. (Attenuation of estrogen receptor-mediated transcription through estrogen-stimulated recruitment of a negative elongation factor, Genes Dev. 2004 18: 2134-2146).*
Bharali, D., et al., "Organically modified silica nanoparticles: A nonviral vector for in vivo gene delivery and expression in the brain", PNAS, vol. 102, pp. 11539-11544 (2005).
Chat, Y., et al., "c.-Fos oncogene regulator Elk-1 interacts with BRCA1 splice variants BRCA1a/1b and enhances BRCA1a/1b-mediated growth suppression in breast cancer cells", Oncogene, vol. 20, pp. 1357-1367 (2001).
Corso, T., et al., "Transfection of tyrosine kinase deleted FGF receptor-1 into rat brain substantia nigra reduces the number of tyrosine hydroxylase expressing neurons and decreases concentration levels of striatal dopamine", Molecular Brain Research, vol. 139, pp. 361-366 (2005).
Sun, H., et al., "Conserved function of RNF4 family proteins in eukaryotes: targeting a ubiquitin ligase to SUMOylated proteins", EMBO, vol. 26, pp. 4102-4112 (2007).
Tischkowitz, M., et al., "The basal phenotype of BRCA1-related breast cancer", Cell Cycle, vol. 5, pp. 963-967 (2006).
Uzunova, K., "Ubiquitin-dependent Proteolytic Control of SUMO Conjugates", JBC, vol. 282, pp. 34167-34175 (2007).
Wang, H., et al., "BRCA1 proteins are transported to the nucleus in the absence of serum and splice variants BRCA1a, BRCA1b are tyrosine phosphoproteins that associate with E2F, cyclins and cyclin dependent kinases", Oncogene, vol. 15, pp. 143-157 (1997).
Fan S., et al., "Role of direct interaction in BRCA1 inhibition of estrogen receptor activity", Oncogene, vol. 20, No. 1, pp. 77-87 (2001).
International Search Report and Written Opinion of the International Searching Authority, mailed Jun. 8, 2012 (Application No. PCT/US2009/06222, filed Nov. 21, 2008).

\* cited by examiner

*Primary Examiner* — Suzanne M Noakes
*Assistant Examiner* — Jae W Lee
(74) *Attorney, Agent, or Firm* — Ping Wang; Andrews Kurth, LLP

(57) ABSTRACT

Assays using binding studies involving function of BRCA1a protein have use for diagnosis and for evaluation of possible tumorogenicity of agents, particularly estrogenic agents. The assays do not rely on use of a probe for only specific sequences, but on effects of known and unknown or not previously studied sequences (consequence of genetic changes) or posttranslational modification of BRCA1 proteins (as a consequence of epigenetic changes) as seen in hereditary and sporadic cancers.

2 Claims, 3 Drawing Sheets
(1 of 3 Drawing Sheet(s) Filed in Color)

BRCA1 FUNCTION-BASED CELLULAR ASSAYS

This application takes priority from U.S. Provisional Application 61/193,371 filed Nov. 21, 2008.

FIELD AND BACKGROUND OF THE INVENTION

This invention relates to assays for evaluating tumor factors which affect breast cancer. The assays for Ubc9 binding are particularly useful for evaluation of tumor activity or expected activity. The methods of the invention are also useful for identifying tumorogenic agents. The methods of the invention are also useful for identification of mutations of a naturally occurring short form of BRCA1 protein named BRCA1a which is expressed at reduced levels or undetectable in high grade breast and ovarian cancers.

BRCA1 and BRCA1a are two proteins that differ in the size and are products of the BRCA1 gene. BRCA1 (breast cancer 1) is a human gene, some mutations of which are associated with a significant increase in the risk of breast cancer (early onset), as well as other cancers. BRCA1 belongs to a class of genes known as tumor suppressors, which maintains genomic integrity to prevent uncontrolled proliferation.

Inherited mutations of the breast cancer susceptibility gene 1 (BRCA1) confer a high risk for the development of estrogen (E2) dependant breast and ovarian cancers. The underlying basis for its tissue specific tumor suppressor function remains poorly understood. Multiple naturally occurring isoforms of BRCA1 are present in different tissues with varying expression levels that encode proteins missing all or part of exon 11. BRCA1a/p110 and BRCA1b/p100 form two of the four major splice variants present in normal, breast and ovarian cancer cells. Both BRCA1a and BRCA1b differ from BRCA1 in having a deletion of the majority of exon 11 sequences (within amino acids (aa) 263-1365). BRCA1b has an additional deletion of exons 9 and 10 sequences and they code for 110 kDa/100 kDa proteins (FIG. 1). BRCA1 and its splice variants are multifunctional proteins that interact with several proteins which regulate a number of biological activities like transcriptional activation/repression, cell-cycle regulation, growth/tumor suppression, apoptosis, DNA repair, genomic stability, steroid hormone receptor signaling, ubiquitination and sumoylation but many of these functions are not tissue specific. Women carrying BRCA1 mutations develop breast tumors that are triple negative (TN) suggesting that hormonal factors play a critical role in the development of these cancers. TN breast cancers account for only about 15% of all breast cancers, they represent a higher percentage of breast cancers arising in premenopausal women and in African American women. currently there are no targeted therapies available for these cancers (14). There is significant overlap between TN breast cancers and BRCA1 associated breast cancers both histologically as well as transcriptionally, which suggests that dysfunction in the BRCA1 pathway may be responsible for the development of these cancers. Estrogen receptor (ERα) signaling has been implicated in the development of BRCA1 associated tissue specific tumorogenesis.

The majority of BRCA1-related breast cancers are ER-negative and more prevalent in younger African American women and pre-menopausal women with breast cancers. (Tischkowitz M D, Foulkes W D: The basal phenotype of BRCA1-related breast cancer: past, present and future. Cell Cycle 5: 963-7, 2006.). Based on recent findings it is shown that lack of BRCA1 results in ER-negative tumors due to sumoylation of ERα resulting in transcriptional silencing of ERα expression. BRCA1 proteins may be an integral part of the sumoylation machinery that function to regulate the overall sumoylation activity of ERα activity in breast and ovarian cancer cells similar to the RNF4 family of RING-finger E3 ubiquitin ligase (Sun H, Leverson J, Hunter T: Conserved function of RNF4 family proteins in eukaryotes: targeting a ubiquitin ligase to SUMOylated proteins. EMBO 26: 4102-12, 2007.). We can also speculate that BRCA1 belongs to the family of SIM-containing RING-finger proteins. (Uzunova K, Gottsche K, Miteva M, Weisshaar S, Glanemann C, Schnellhardt M, Niessen M, et al.: Ubiquitin-dependent Proteolytic Control of SUMO Conjugates. J Biol Chem 282: 34167-75, 2007) that induce turnover of ERα following its sumoylation. The role of BRCA1 may be to fine tune ERα transcriptional activation in response to rapid changes in E2 levels. Assays such as that shown in FIG. 1 that measure the extent to which BRCA1 dysfunction results in ERα-positive and negative breast cancers are needed.

FIG. 1 gives models showing how BRCA1 dysfunction in regulating the E2-induced ER α-activation/repression by SUMO-dependent/independent activities of Ubc9 results in (a) ERα-negative and (b) ERα-positive breast cancers.

Post translational modification of transcriptional factors is important for regulated gene expression. SUMO-1, a 98 amino acid polypeptide, is covalently attached to lysine residues in proteins. Post-translational modification by SUMO has effects on the stability, localization, protein-protein interactions and transcriptional regulation (activation or repression). In most cases sumoylation of transcription factors (eg. HDAC1, p300/CBP, CtBP, STAT1, etc.) and Histone 4 inhibits transcription by promoting recruitment of co-repressors like HDAC complex. SUMO-1 also binds to the SUMO binding motifs in BRCA1 and represses BRCA1-mediated transcription in a sumo-independent manner by recruiting HDAC. The SBM is different from the SUMO-1 modification consensus sequence ($\Psi$-K-X-E) which is found in SUMO-1 substrates proteins (Table 1 and FIG. 1a/b). SBM binds SUMO non-covalently but $\Psi$-K-X-E does not bind to SUMO-1 non-covalently. It appears to bind Ubc9 non-covalently for covalent SUMO attachment. Most SUMO-modified proteins contain the tetra peptide motif $\Psi$-K-X-D/E where $\Psi$ is a hydrophobic residue, K is the lysine conjugated to SUMO, X is any amino acid, and D or E is an acidic residue. A wide variety of proteins are sumoylated (Table 1). ERα is a nuclear transcription factor that undergoes various types of post translational modifications like phosphorylation, acetylation, ubiquitination, methylation, and sumoylation. ERα is sumoylated at conserved lysine residues within the hinge region only in the presence of E2. PIASI, PIAS3 act as E3 ligases and Ubc9 as E2 SUMO-conjugating enzyme for ERα sumoylation and also modulate ERα transcription independent of SUMO-1 conjugation activity. Mutations that abrogate sumoylation impair ERα dependent transcriptional activation but not its subcellular localization. Ubc9 is the only mammalian E2 conjugating enzyme that is essential for sumoylation. The mutant C93S Ubc9, which prevents SUMO-1 conjugation by preventing the formation of thiolester bond between SUMO-1 and Ubc9, still functions as a co activator for nuclear receptors. Thus there can be sumo-dependent transcriptional activation or repression and sumo-independent transcriptional activation or repression of promoters. A role for post translational modifications in targeting ERα for degradation is poorly understood. A direct correlation has been observed by some between the rate of ERα degradation and its transcriptional activation and treatment of cells with proteosome inhibitor MG132, impaired ERα transcription. Furthermore ERα is ubiquitylated after the first round of transcription which may be needed for subsequent E2-mediated ERα transcription. ERα thus cycles on and off the promoter as long as E2 is present. SUMO-1 was found to suppress BRCA1 mediated transcription of Gadd45 α, p27 KIP1 and p21 WAF1/CIP1 via modulation of promoter occupancy. The only known enzymatic activity that is associated with BRCA1 is its E3 ubiquitin ligase activity, and recently ERα was shown to be a putative substrate for this BRCA1/BARD1 ubiquitin ligase activity. Deleterious BRCA1 RING-finger domain mutations eliminated the ubiquitin ligase activity, but did not eliminate its auto ubiquitination activity indicating a link between tumor suppressor function of BRCA1 and its E3 ligase activity. However all these studies do not uncover the paradox as to why impairment of this E3-ligase activity contributes to ER-negative breast cancers.

Several patents have been issued relating to the BRCA1 gene and protein. U.S. Pat. No. 5,750,400 to Murphy, et al., which is incorporated herein in its entirety, discloses and claims the gene sequences. It also discloses means of identifying certain mutations. U.S. Pat. No. 5,747,282 to Skolnick, et al, which is incorporated herein by reference in its entirety, discloses 17q-linked sequence of a gene predisposing to breast and ovarian cancer. U.S. Pat. No. 5,756,294 to White, et al, which is incorporated herein by reference in its entirety, discloses another cDNA sequence which correlates with susceptibility to breast and ovarian cancer and uses allele-specific oligonucleotides in identifying the particular sequences. U.S. Pat. No. 7,507,800 to van Ommen, et al, which is incorporated by reference herein in its entirety, discloses and claims a diagnostic kit for determining predisposition to breast and ovarian cancer. The test relies on use of probes for particular, previously identified sequences.

BRIEF DESCRIPTION OF THE DRAWINGS

The file of this patent contains at least one drawing executed in color. Copies of this patent with color drawings will be provided by the Patent and Trademark Office upon request and payment of the necessary fee.

SUMMARY OF THE INVENTION

Figure 1A:
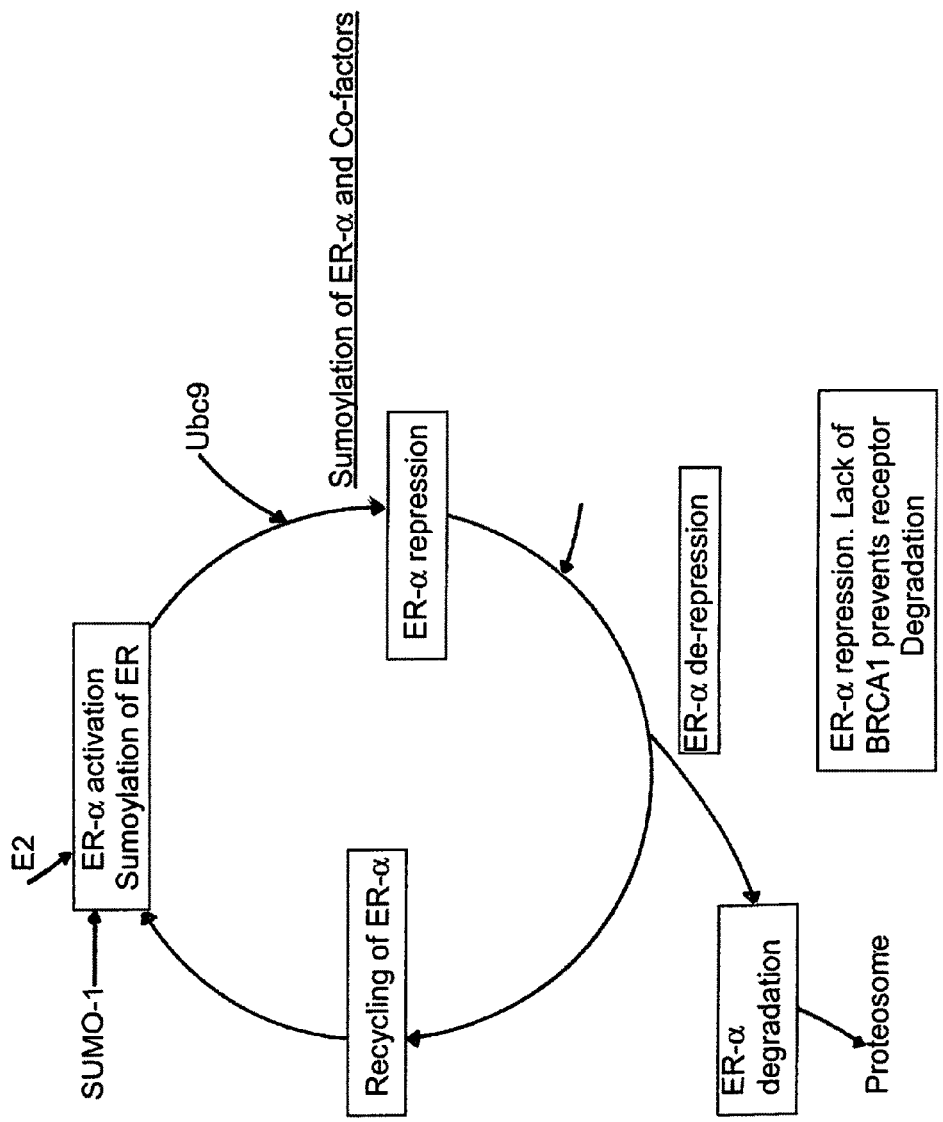
FIG. 1: Shows models of BRCA1 dysfunction in regulating the E2-induced ER α-activation/repression by SUMO-dependent/independent activities of Ubc9 results in (a) ERα-negative and (b) ERα-positive breast cancers.

This invention relates to use of assays for use in guiding gene therapy strategy that involves introducing BRCA1a protein into Triple negative breast cancers, ovarian and prostate cancers to stop tumor development. Some assays of the invention provide binding studies which, in addition to other values, have use for diagnosis and for evaluation of possible tumorogenicity of agents, particularly estrogenic agents. There have previously been no targeted treatments that are effective against TN breast cancers. The signaling pathways that drive proliferation of these cancers are not understood. The advantage of this invention is that it provides a means for testing targeted therapies based on enhancing the degradation of repressed ERα to reinitiate the transcription of estrogen receptor as a method for the treatment of these ER-negative breast cancers. Methods of the invention also make it possible to test effects of environmental agents' on deregulating the levels of Ubc9 and various functions of BRCA1 proteins using the different cell based assays described as a means of evaluating possible tumorogenic effects.

The invention disclosed and claimed herein makes it possible to probe for previously unidentified tumorogenic sequences by identifying effect on Ubc9 inhibition and on whether or not there is binding to Ubc9 which could result in cytoplasmic or nuclear localization of BRCA1 proteins. Hence, the invention does not rely on use of a probe for only specific sequences, but on effects of known and unknown or not previously studied sequences (consequence of genetic changes) or posttranslational modification of BRCA1 proteins (as a consequence of epigenetic changes) as seen in hereditary and sporadic cancers.

DETAILED DESCRIPTION OF THE INVENTION

BRCA1a differs from BRCA1 in having in frame deletions of residues 263-1365. The anti-tumor activity of BRCA1 needs the presence of another tumor suppressor, Rb but not p53. This major discovery provides new avenues in the future for the treatment of one of the biggest needs in breast cancer research. A consensus SUMO modification site in the amino-terminal region of BRCA1/1a/1b proteins and mutation in this potential SUMO acceptor site (lysine (K) 109 to arginine (R)) which impaired their ability to bind and repress ligand dependent ERα transcriptional activity in breast cancer cells has been identified.

It has now been found that a SCS (SUMO-1 modification consensus sequence) in the conserved amino terminal RING finger domain of BRCA1/1a/1b proteins and mutation in this SUMO acceptor site and cancer-predisposing mutation C61G impaired their ability to both interact with ERα and SUMO-E2-conjugating enzyme Ubc9 as well as modulate Ubc9 mediated SUMO-dependant/independent E2 induced ERα transcriptional activation in breast cancer cells. Ubc9 is a newly discovered player in the E2-induced ERα regulation by BRCA1 proteins. The results indicate BRCA1/1a/1b proteins (but not the mutant wherein lysine (K) at 109 is replaced by arginine (R)) to be putative SUMO-1 and Ubc9-dependent E3 ubiquitin ligases that bind and recruit the E2 ubiquitin conjugating enzyme Ubc9 to ERα and facilitate the ubiquitination and proteosome dependent degradation of ERα in an estrogen dependent manner. These findings suggest a novel mechanism whereby BRCA1 fine tunes the dynamic interplay between SUMO dependent/independent activities of Ubc9 on E2 induced ERα regulation and dysfunction in this activation-repression switch due to lack of BRCA1 results in ER-negative and ER-positive breast cancers. The results from these studies shed light on the enigma as to why BRCA1 dysfunction leads to ER-negative breast cancers.

DEFINITIONS

ER-negative refers to a specific subtype of breast cancer that does not express the genes for estrogen receptor GFP is composed of 238 amino acids (26.9 kDa), originally isolated from the jellyfish *Aequorea victoria* that fluoresces green when exposed to blue light. In modified forms it has been used to make biosensors, and many animals have been created that express GFP as a proof-of-concept that a gene can be expressed throughout a given organism. The GFP gene can be introduced into organisms and maintained in their genome through breeding, or local injection with a viral vector which can be used to introduce the gene. Due to the potential for widespread usage and the evolving needs of researchers, many different mutants of GFP have been engineered. One such is EGFP.

Ormosil is a shorthand phrase for organically modified silica or organically modified silicate. This technology has been demonstrated as a nonviral vector to successfully deliver DNA loads to specifically targeted cells in living animals. Confirmation of results demonstrated that new DNA was working and expressed genes in the animal.

Triple-negative breast cancer refers to a specific subtype of breast cancer that does not express the genes for estrogen receptor (ER), progesterone receptor (PR) or Her2/neu. This subtype of breast cancer is clinically characterized as more aggressive and less responsive to standard treatment and associated poorer overall patient prognosis. It is diagnosed more frequently in younger women, women with BRCA1 mutations and is more frequently found in premenopausal onset patients and in patients of African-American and Hispanic ethnic populations at all ages.

Small Ubiquitin-like Modifier or SUMO proteins are a family of small proteins that are covalently attached to and detached from other proteins in cells to modify their function. SUMOylation is a post-translational modification involved in various cellular processes, such as nuclear-cytosolic transport, transcriptional regulation, apoptosis, protein stability, response to stress, and progression through the cell cycle. There are 3 confirmed SUMO isoforms in humans; SUMO-1, SUMO-2 and SUMO-3.

SCS stands for SUMO consensus sequence which is recognized by Ubc9.

BRCA1 associated RING domain 1, also known as BARD1, is a human gene. BARD1 interacts with the N-terminal region of BRCA1. The BARD1/BRCA1 interaction is disrupted by tumorigenic amino acid substitutions in BRCA1, implying that the formation of a stable complex between these proteins can be an essential aspect of BRCA1 tumor suppression. BARD1 may be the target of oncogenic mutations in breast or ovarian cancer (UBC9) Ubiquitin-conjugating enzymes, also known as E2 enzymes and more rarely as ubiquitin-carrier enzymes, perform the second step in the ubiquitination reaction that targets a protein for degradation via the proteasome. The ubiquitination process covalently attaches ubiquitin, a short protein of 76 amino acids, to a lysine residue on the target protein. Once a protein has been tagged with one ubiquitin molecule, additional rounds of ubiquitination form a polyubiquitin chain that is recognized by the proteasome's 19S regulatory particle, triggering the ATP-dependent unfolding of the target protein that allows passage into the proteasome's 20S core particle, where proteases degrade the target into short peptide fragments for recycling by the cell.

pTRE-HA is a tetracycline response plasmid that can be used to tag a gene of interest with an HA epitope and then to induce expression of the tagged protein.

Materials and Methods
Cell Culture

MCF-7, T47 D and COS-1 cells were obtained from American Type Culture Collection (Rockville, Md., USA). MCF-7 cells were cultivated in MEM with 10% Fetal bovine serum, 1% penicillin and streptomycin, 10 mg/ml Insulin. T47D were grown in DMEM with 10% Fetal bovine serum, 0.2 units/ml Insulin, 1% Penicillin Streptomycin and 0.15% sodium bicarbonate.

Expression Constructs

Figure 1B:
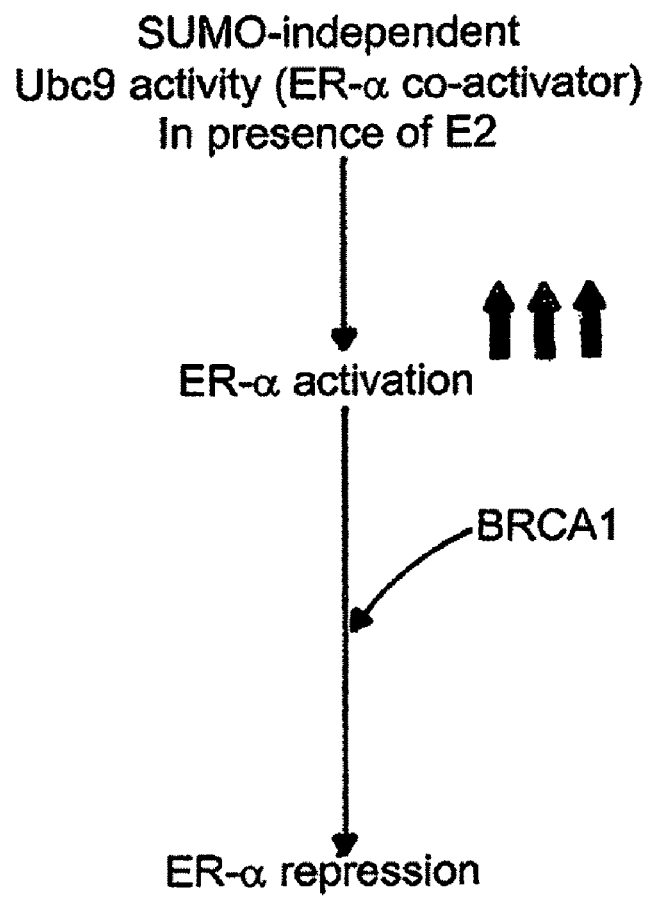

Expression plasmid encoding full-length BRCA1 in pcDNA3, pSG5-ERα and ERE-TK-luciferase reporter, pcDNA3 Ubc9, pcDNA3 Ubc9 C93S both V5-tagged and pcDNA3 6xHis/SUMO-1, and pGEX-Ubc9 were generously provided by Dr. Michael Erdos (National Human Genome Research Institute, Bethesda, Md., USA), Prof. M. G. Parker (London, U.K.), Prof. Ron Hay and Dr. Ellis Jaffrey (University of Dundee, U.K.), and Dr. Michael J. Mutanis (John Hopkins University), respectively. The pCDNA3 BRCA1a & pCDNA3 BRCA1b plasmids have been described previously (Wang H, Shao N, Ding O M, Cui J, Reddy E S P, Rao V N: BRCA1 proteins are transported to the nucleus in the absence of serum and splice variants BRCA1a, BRCA1b are tyrosine phosphoprotein that associate with E2F, cyclins and cyclin dependent kinases. The cDNAs for BRCA1 1-182 were constructed by PCR cloning and sub cloning into the pCMV-Tag 2 vector (Stratagene, La Jolie, Calif., USA) according to the directions. This vector allows expression of BRCA1 protein with an N-terminal FLAG sequence. BRCA1, 1a, 1b, BRCA1 1-182 point mutants 1, and 4 (see FIG. 1b and text) were constructed using Quick change site directed Mutagenesis kit (Stratagene).

GST-Pull Down Assays

GST-Ubc9 and GST-ERα (337-379) were expressed and purified from E. coli as described previously (Wang H, Shao N, Ding O M, Cui J, Reddy E S P, Rao V N: BRCA1 proteins are transported to the nucleus in the absence of serum and splice variants BRCA1a, BRCA1b are tyrosine phosphoprotein that associate with E2F, cyclins and cyclin dependent kinases. Oncogene 15, 143-157: 1997.). For in vitro protein binding assay 35 S-Methionine-labeled in vitro translated full length BRCA1, BRCA1a (Chai Y L, Cui J, Chipitsyna G, Liao B, Lui S, Aysola K et al.: C-Fos oncogene regulator Elk-1 interacts with BRCA1 splice variants BRCA 1a/1b and enhances BRCA1a/1b mediated growth suppression in breast cancer cells. Oncogene 20: 1357-1367, 2001.), BRCA1b, BRCA1 Mut#1, BRCA1 Mut#4, BRCA1 1-182, BRCA1 1-182 Mut#1 and BRCA1 1-182 Mut 4 proteins were diluted in binding buffer (20 mM Tris-HCl (pH7.5), 150 mM NaCl, 0.1% Tween 20). The proteins were precleared with GSH beads for 30 min and then incubated with GST or various GST-ER (337-379) proteins beads for 2 hours at 4° C. The beads were then washed three times with binding buffer followed by elution of the bound proteins with SDS sample buffer and loaded on a 15% SDS-PAGE. The gels were fixed, treated with enhance, dried and exposed 9 to X-ray films) and scanned using a Fuji BioImaging analyzer. Competition studies using Ubc9 and Ubc9C93S as competitors were performed as described above except that 50 ul of BRCA 1-182 translated proteins were pre-incubated with increasing amounts of (40, 60, and 80 ul) of in-vitro translated Ubc9 and Ubc9C93S proteins before the addition of GST-ER (337-379) beads. The gels were fixed, treated with enhancer, dried, exposed and scanned using a phospho-Imager Immunoflourescence Staining To study the co-localization of endogenous and exogenous BRCA1 and BRCA1a with Ubc9 in vivo, MCF-7 cells were cultured on glass cover slips in six-well plates overnight. Sub confluent cells were either used as such or transfected overnight with the indicated expression plasmid (1.5 µg BRCA1 or BRCA1a) using Lipofectamine and incubated in fresh/well medium for 24 hours. Cells were then washed with PBS, fixed in ice cold methanol for 5 minutes, and then washed with PBS. The cells were then blocked with 10% Bovine serum albumin in PBS for 30 minutes at room temperature, followed by incubation with Image-iT FX signal enhancer (136933, Invitrogen, Carlsbad, Calif., USA) for 30 minutes; Incubated with either Anti-BRCA1 (Ab-1) Mouse mAb (MS110) (OP92, EMD Chemicals, Gibbstown, N.J., USA) or primary mouse monoclonal GFP antibody (sc-9996, Santa Cruz, Calif., USA, 1:200 dilution in 1.5% BSA/PBS) and rabbit polyclonal Ubc9 Antibody (sc-10759, Santa Cruz, Calif., USA, 1:200 dilution in 1.5% BSA/PBS) at 25° C. for 1 hour. This was followed by incubation with secondary antibody Alexa Fluor® 488 goat anti-mouse IgG (H+L) highly cross-adsorbed (11034, Invitrogen, Carlsbad, Calif., USA, 1:200 dilution in 1.5% BSA/PBS) and Alexa Fluor® 568 goat anti-rabbit IgG (H+L) highly cross-adsorbed (11036, Invitrogen, Carlsbad, Calif., USA, 1:200 dilution in 1.5% BSA/PBS) for 50 minutes. The cells were rinsed with PBS and cover slips mounted in Ultra Cruz™ mounting medium with 4,6-diamidino-2-phenylindole (DAPI) (sc-24941, Santa Cruz, Calif., USA). The stained cells were examined using an Olympus 1X71 microscope, equipped with 100x/1.25 oil ph immersion objectives. Composite filter cubes were used for the FITC, DAPI and TRITC fluorescence, respectively. The pictures were captured with a Moticam 3000 camera.

Co-Immunoprecipitation

To study the association of Ubc9 with BRCA1a protein proliferating COS-1 cells at about 70% of confluence in 100-mm petridishes were transfected for 48 hrs with (18 μg of plasmid DNA/dish), using Fugene 6. The cells were harvested and whole-cell extracts was prepared using ERα RIPA buffer as described (22). The extracts were incubated overnight at 4° C. with 10 ul of anti-FLAG M2 affinity gel (Sigma Aldrich Inc). After low speed centrifugation, the agarose beads were washed with PBS and the pellet was suspended in boiling SDS sample buffer and subjected to 4-20% SDS-PAGE followed by Western blot analysis using Anti-Flag/Anti V5 antibodies.

Western Blot Analysis

For western blot analysis total protein lysates were electrophoresed on a 4-20% SDS polyacrylamide gradient gel. The proteins were transferred onto nitrocellulose membranes and probed with anti-FLAG (M2 mouse monoclonal (Sigma, 1:500 dilution) or anti-V5 mouse monoclonal (Invitrogen, 1:2000 dilution) antibodies. Antibody binding was detected by using the enhanced chemiluminescence system (ECL), with PAGE RULER™ plus pre-stained protein ladder (Fermentas) as molecular weight standards.

Assay for the Effect of E2 on ERα Transcriptional Activation

T47D cells ($5 \times 10^5$) were plated in 6-well plates for 24 hours. The cells were washed twice in PBS followed by the addition of phenol red free DMEM containing 5% charcoal-stripped FBS for 48 hrs before transfection. The cells were transfected with 1 μg of each of the indicated plasmids (with a total of 2.5 μg DNA) using lipofectamine 2000 (Life Technology, USA). The cells were induced with 1 μM of E2 4 hours after transfections, harvested after an additional 40 hrs and assayed for luciferase activity following the manufacturer's instructions. Each set of experiments was performed in triplicate and repeated a least three times.

Analysis of In Vivo E2 Induced SUMO-1 and Ubc9-Dependent E3 Ubiquitin Ligase Activity of BRCA1 in COS-1 Cells Briefly, COS-1 cells were plated at a density of $1 \times 10^6$ cells per 100-mm tissue culture dishes. After 24 hours cells were cultured under sterol-free conditions in phenol-red-free medium (Life Technology) containing 5% charcoal-stripped fetal bovine serum for 48 hours. Cells were transfected with 7 μg of plasmid DNA, (Total of 21 μg DNA) using Fugene 6 (Roche Molecular Biochemicals, Indianapolis, Ind., USA) according to the manufacturer's protocol. After 8 hrs, the cells were incubated with 100 nM E2 for 24 hrs. Cells were then harvested in modified RIPA buffer (50 mM Tris-Hcl, pH 7.8; 150 mM NaCl; 5 mM EDTA; 0.5% Triton X-100; 0.5 Nonidet P-40; 0.1% sodium deoxycholate) with protease inhibitors in presence of 20 mM NEM (N-Ethylmalemide). Lysates were syringed on ice with a 22-gauge syringe and centrifuged to separate insoluble proteins. SDS sample buffer was added to lysates and loaded on a 4-20% gradient gel. Membrane was transferred onto a polyvinylidene diflouride membrane overnight and then blocked by incubation with 5% BSA and 0.001% Tween-20 overnight. ERα was detected with mouse monoclonal anti ERα antibody (1:100 dilution) and secondary anti mouse HRP-conjugated secondary antibody 1:4000 dilution for 1 hr at room temperature. The membrane was washed and the results were analyzed using LAS-IMAGE reader 3000.

BRCA1 RING Domain Cancer-Predisposing Mutation C61G Disrupts Ubc9 Binding

BRCA1 C61G mutation observed in breast cancer patients has lost both BRCA1/BARD ubiquitin ligase activity as well as ability to inhibit ERα activity in breast cancer cells (33). We did not observe any significant binding of in vitro translated full length BRCA1 Mutant #4 (C61G) to Ubc9 using GST capture assays (Table 1a). These results indicate a link between the loss of BRCA1 ubiquitin ligase activity, loss of ERα repression and Ubc9 binding.

Assays of the invention have several uses. Using methods of the invention, the BRCA1a DNA and protein, as well as other possible therapeutic agents, may be evaluated for clinical use in treatment of particular triple negative breast cancers which are highly prevalent in premenopausal women and African American and Hispanic women of all ages and in ovarian cancers, prostate cancers, pancreatic cancers and other malignancies related to mutations of BRCA1a by determining the response in binding assays and cultures. Novel non-viral transfection vectors expressing BRCA1a may be used for in vivo gene therapy into ER-negative tumors. Using methods of the invention, TN breast cancer cells or tumor stem cells may be studied for suppression of the tumorgenic phenotype both in vitro and in xenograft mouse models. These nano-BRCA1a vectors can be used for gene therapy in patients with TN malignancies The new BRCA1 function-based cellular assays detect how estrogen receptors activity in cancers is modulated. A SCS (SUMO-1 modification consensus sequence) in the amino terminal RING finger domain of BRCA1/1a/1b proteins has been identified. Mutation in this SUMO acceptor site and cancer-predisposing mutation C61G found in patients with breast cancer impair their ability to both interact with ERα (estrogen receptor alpha) and SUMO-E2-conjugating enzyme Ubc9 as well as modulate Ubc9-mediated SUMO-dependant/independent E2 (Estradiol) induced ERα transcriptional activation in breast cancer cells. The recognition of the role of Ubc9 (E2-conjugating enzyme) in the E2-induced ERα regulation by BRCA1 proteins is of importance in the new means of evaluation in the methods of the invention. This is the first showing that Ubc9 participates in both sumoylation as well as ubiquitination of ERα by BRCA1 proteins. Results indicate BRCA1/1a/1b proteins, but not K109R mutations, are the putative SUMO-1 and Ubc9-dependent E3 ubiquitin ligases that bind the E2 ubiquitin conjugating enzyme Ubc9 and ERα to facilitate the ubiquitination and proteosome dependent degradation of ERα in an estrogen dependent manner. These findings indicate a novel mechanism whereby BRCA1 modulates the dynamic interplay between SUMO dependent/independent activities of Ubc9 on E2 induced ERα regulation and dysfunction. This activation/repression switch controlled by a lack of BRCA1 results in either ER-negative and ER-positive breast cancers. Previously there are no cell based functional BRCA1 assays for ER-positive and ER-negative/triple negative breast and ovarian cancers. The cell-based assays that described here take advantage of the observation that BRCA1 dysfunction results in ER-positive/negative, triple negative breast and ovarian cancers. We show that BRCA1 functions as a RING E3 ubiquitin ligase for ER-alpha in presence of Ubc9 thus opening up a new pathway/function for BRCA1 proteins.

TABLE 1

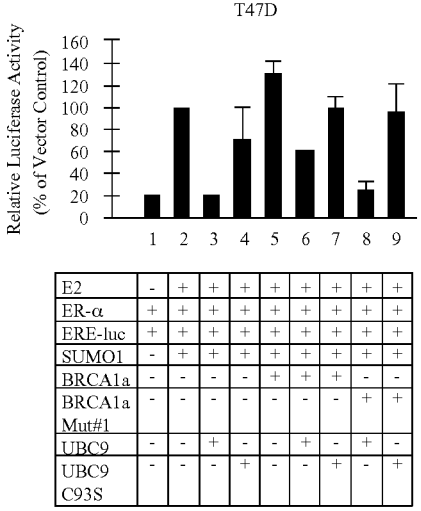

BRCA1a, but not Mut#1 relieves ERα repression by Ubc9 in breast cancer cells. T47D cells were transfected with ERE-Luciferase reporter and SUMO-1 and BRCA1a, BRCA1a Mutant#1 in presence of UBC9 or UBC9 C93S or without as indicated. After recovery, cells were treated with E2 (1 μM) or ethanol vehicle (-). Forty-eight hours after transfection, luciferase activity was analyzed by using a luciferase assay kit. The data are presented as the mean ± s.d. of three independent experiments performed in triplicate.

Three cell based assays are available.

Assay #1: Cell based assay to screen small molecules that mimic BRCA1 function or activate the BRCA1 pathway in estrogen receptor-negative or triple negative breast cancer cells.

Methodology for cell based assay#1: Assay for the effect of E2 on ERα transcriptional activation T47D cells (5×10$^5$) were plated in 6-well plates for 24 hours. The cells were washed twice in PBS (phosphate buffered saline) followed by the addition of phenol red free DMEM containing 5% charcoal-stripped FBS for 48 hrs before transfection (The cells were transfected with 1 μg of each of the indicated plasmids (ERE-luciferase reporter containing the vitellogenin A2 ERE in plasmid pGL2 and pSG5 ERα were generous gifts from Professor M. G. Parker (Henttu et al., 1997), pCDNA3 SUMO-1 and pCDNA3 Ubc9 were provided by Professor Ron Hay (Hay, 2005), and pCDNA3 BRCA1a/1b has been previously described by us {Wang et al., 1997}) with a total of 2.5 μg DNA using lipofectamine 2000 (Life Technology, USA). The cells were induced with 1 μM of E2 4 hours after transfections, harvested after an additional 40 hrs and assayed for luciferase activity which is quantified by integrating the light intensity over a specified time period, following the manufacturer's instructions (Promega Corporation, Wisconsin, USA). Each set of experiments was performed in triplicate and repeated a least three times.

The expression of BRCA1a unlike BRCA1a Mutant #1 relieved the E2-dependant ERα transcription repression by Ubc9 in T47D breast cancers cells. These results indicate BRCA1 proteins antagonize SUMO-1 and Ubc9-dependent transcription repression of ERα in T47D breast cancer cells. The scenario with reference to repression of ERα in the absence of BRCA1 is very similar to what is seen in ERα-negative/TN breast cancer cells where there is undetectable levels of BRCA1. Any drug that relieves more than 50% of the control will be considered as potential candidates that mimic the function of BRCA1 in ERα-negative/TN breast cancers.

Assay #2: Screening small molecules that mimic BRCA1 function or activate the BRCA1 pathway in estrogen receptor-positive breast cancer cells.

TABLE 2

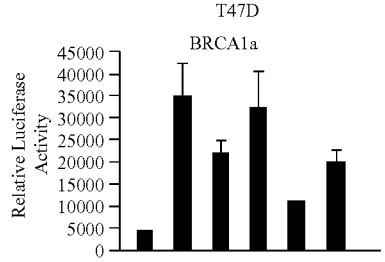

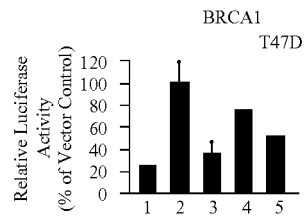

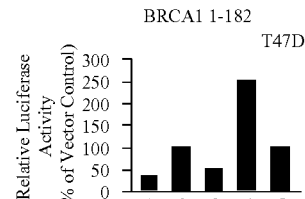

Table 2 legend.
BRCA1a/1b but not Mut#1 inhibit E2-induced ERα activity by Ubc9 C93S (SUMO-independent) in breast cancer cells. T47D cells were transfected with ERE-Luciferase reporter and UBC9 C93S and BRCA1b, BRCA1a or BRCA1a Mut#1 as indicated.
After recovery, cells were treated with E2 (1 μM) or ethanol vehicle (-). pCMV Tag2 and PCDNA3 vectors were also included for normalization of the transfections. Forty-eight hours after transfection, luciferase activity was analyzed by using a luciferase assay kit. The data are presented as the mean ± s.d. of three independent experiments performed in triplicate. (b) BRCA1 and BRCA1 1-182 but not Mut#1 and Mut#4 inhibit E2-induced ERα activity by Ubc9 C93S (SUMO-independent) in breast cancer cells.
T47D cells were transfected with ERE-Luciferase reporter and UBC9 C93S and BRCA1, BRCA1 Mut#1, BRCA1 Mut#4, BRCA1 1-182, BRCA1 1-182 Mut#1 or BRCA1 1-182 Mut#4 as indicated. After recovery, cells were treated with E2 (1 μM) or ethanol vehicle (-). pCMV Tag2 and PCDNA3 vectors were also included for normalization of the transfections. Forty-eight hours after transfection, luciferase activity was analyzed by using a luciferase assay kit. The data are presented as the mean ± s.d. of three independent experiments performed in triplicate.

Methodology of Assay #2: This is an assay for the effect of E2 on ERα transcriptional activation T47D cells (5×10⁵) were plated in 6-well plates for 24 hours. The cells were washed twice in PBS followed by the addition of phenol red free DMEM containing 5% charcoal-stripped FBS for 48 hrs before transfection. The cells were transfected with 1 µg of each of the indicated plasmids (with a total of 2.5 µg DNA) using lipofectamine 2000 (Life Technology, USA). The cells were induced with 1 µM of E2 4 hours after transfections, harvested after an additional 40 hrs and assayed for luciferase activity following the manufacturer's instructions. Each set of experiments was performed in triplicate and repeated a least three times.

Ubc9 has been shown previously to regulate ERα transcription independent of its sumoylation activity. Ubc9 has been found to be expressed at elevated levels in several metastatic cancers. This assay was used to evaluate the effect of BRCA1, BRCA1a, BRCA1b, BRCA1/1a Mutant #1, BRCA1/1a Mut#4, BRCA1 (aa 1-182), BRCA1 (aa 1-182) Mutant #1 and Mut#4 on E2-induced ERα activation by a catalytically inactive form of Ubc9, Ubc9/C93S using an ERE-luciferase reporter in T47D breast cancer cells. It was found that BRCA1/1a and BRCA1 (aa 1-182), unlike their respective Mut #1 and Mut#4, inhibit E2-mediated ERα transcription activation by Ubc9/C93S in breast cancer cells. (Table 1 a and b). Results produced from cell based assay 2 can be used to screen small molecules that can inhibit the mutant Ubc9-mediated activation of ERα in ER-positive breast cancer cells. Any small molecule that can inhibit 50% and above of the control will considered as potential candidates that mimic the function of BRCA1 in ERα-negative/TN breast cancers.

TABLE 3

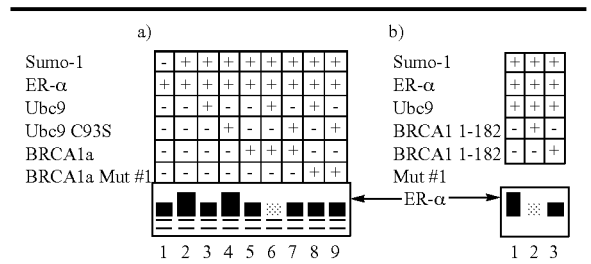

The depiction above shows degradation of E2-induced sumoylated ERα by (a) BRCA1a, (b) BRCA1 1-182 but not Mut#1 occurs only in the presence of Ubc9 or Ubc9C93S Cell Based Assay#3
Methodology for cell based assay 3: Analysis of in vivo E2 induced SUMO-dependent E3 Ubiquitin ligase activity of BRCA1 in COS-1 cells to screen small molecules that mimic the function of BRCA1 or activate the BRCA1 pathway in estrogen receptor-negative breast cancer cells.

COS-1 cells were plated at a density of 1×10⁶ cells per 100-mm tissue culture dishes. After 24 hours cells were cultured under sterol-free conditions in phenol-red-free medium (Life Technology) containing 5% charcoal-stripped fetal bovine serum for 48 hours. Cells were transfected with 7 µg of plasmid DNA, (Total of 21 µg DNA) using Fugene 6 (Roche Molecular Biochemicals, Indianapolis, Ind., USA) according to the manufacturer's protocol. After Sirs, the cells were incubated with 100 nM E2 for 24 hrs. Cells were then harvested in modified RIPA buffer (50 mM Tris-Hcl, pH 7.8; 150 mM NaCl; 5 mM EDTA; 0.5% Triton X-100; 0.5 Nonidet P-40; 0.1% sodium deoxycholate) with protease inhibitors in presence of 20 mM NEM (N-Ethylmalemide). Lysates were syringed on ice with a 22-gauge syringe and centrifuged to separate insoluble proteins. SDS sample buffer was added to lysates and loaded on a 4-20% gradient gel. Membrane was transferred onto a polyvinylidene diflouride membrane overnight and then blocked by incubation with 5% BSA and 0.001% Tween-20 overnight. ERα was detected with mouse monoclonal anti ERα antibody (1:100 dilution; Santa Cruz Biotechnology, Calif., USA) and secondary anti mouse HRP-conjugated secondary antibody 1:4000 dilution for 1 hr at room temperature. The membrane was washed and the results were analyzed using LAS-IMAGE reader 3000.

The ubiquitin pathway is important for degradation of ERα and is also required for efficient ERα trans-activation. The only known biochemical activity associated with BRCA1 is its E3 ubiquitin ligase activity. BRCA1 and the BARD1 proteins form a complex with the E2-conjugating enzyme UbCH5c that can catalyze this activity in vivo. Recently, ERα has been identified as a putative substrate for the BRCA1/BARD1 ubiquitin ligase. Cancer pre-disposing mutations within the RING domain of BRCA1 were found to impair the BRCA1/BARD1 ERα ubiquitination as well as ERα transcriptional repression suggesting a link between loss of BRCA1 ligase activity and BRCA1-associated tissue-specific breast and ovarian cancers. Ubc9 was initially linked to ubiquitination due to its homology with ubiquitin-conjugated enzymes. In fact addition of purified human Ubc9 resulted in in vitro ubiquitination of activating transcription factor 2. Recent results have found Ubc9 to be involved in sumoylation of several target proteins. Since BRCA1 is an E3-ubiquitin ligase it is pertinent to understand if its ability to relieve the transcriptional repression of ERα is due to degradation of ERα. The ERα protein expression was analyzed in E2-induced Cos-7 cells that were transiently transfected with constructs encoding ERα, SUMO-1 Ubc9 or Ubc9/C93S in the absence and presence of BRCA1a/BRCA1 (aa 1-182) or Mutant#1. Transfected cells were lysed in the presence of N-ethylmaleimide (NEM) an inhibitor of SUMO-1 hydrolase and subjected to western blot analysis using ERα antibody. Anti-ERα antibody detected a major band of 66 kD which corresponds to ERα. The ERα band almost disappeared in Cos-7 cells transfected with SUMO-1, Ubc9 and BRCA1a and this band was faint in presence of Ubc9/C93S mutant. No such ligand induced, Ubc9 or Ubc9/C93S mediated ERα degradation was seen in presence of SUMO-1 alone or Mutant #1. These results indicate a novel mechanism where the E3-ubiquitin ligase BRCA1, binds and recruits E2 SUMO-conjugating enzyme Ubc9 to ERα and facilitates its ubiquitination and proteosome-dependent degradation in an estrogen-dependent manner. Thus, it is seen that E2 SUMO-conjugating enzyme has been shown to participate both in sumoylation as well an ubiquitination depending on the interacting partners. These results indicate a role for BRCA1 RING finger E3 ubiquitin ligase in bringing together ERα substrate and Ubc9 E2 enzyme to mediate the degradation of ERα via the ubiquitin-proteasome pathway in normal breast mammary cells and inhibition of this function due to lack of BRCA1 can prevent receptor turn over resulting in ER-negative breast cancers. Since ERα was found to be degraded even in the presence of a sumo-defective mutant Ubc9 suggesting a sumoylation independent function of Ubc9 in the degradation of ERα. Hence, Ubc9 is shown to be a dual specificity E2-ubiquitin/sumo conjugating enzyme for ERα and BRCA1 regulates this molecular switch.

It is possible to use a pEGFP vector that provides a revolutionary system for monitoring BRCA1a protein expression and subcellular localization in vivo and in real time. EGFP, an enhanced red-shifted variant of GFP exhibits higher expression and fluorescence intensity compared to wild type GFP.

The full length BRCA1a cDNA has now been cloned in the XhoI site of pEGFP-C1 plasmid available with us from CLONTECH. The protein is expressed as an N-terminal CFP tagged fusion permitting real time live imaging using confocal microscope or detection in live cells via GFP fluorescence or western blot analysis as described previously. The procedure for the preparation and characterization of ORMOSIL/DNA nanoparticles is carried out as described previously (Bharali, PNAS, 2005(102): p. 11539-11544). The micelles are prepared by dissolving a fixed quantity of the aerosol OT and 1-butanol in double distilled water as described in (Corso et. al., Molecular Brain Research 2005 (139) 361-366).

It has now been demonstrated that BRCA1 splice variant BRCA1a can significantly inhibit the growth of ER positive MCF-7, TN CAL51 breast cancer cells, hormone independent-ES-2 ovarian and PC-3 prostate cancer cells. Since BRCA1a lacks majority of exon 11 sequences (263-1365) which includes one of the Rb binding domains (amino acid-304-394) and p53 interaction domains (amino acid 224-503), c-myc (amino acid 433-511), gamma tubulin (amino acid 504-803), STAT1 (amino acids 502-802), RAD 51 (amino acid 758-1064), RAD50 (amino acid 341-748) binding domains and nuclear localization signal sequences suggests that this region of exon 11 is dispensable for the tumor suppressor function of BRCA1 protein. It is probable that mutations that are present in the patient within the exon 11 region (residues 263-1365) may not be functionally significant for the tumor suppressor activity of this gene. Recently expression of an amino-terminal BRCA1 deletion mutant in adenoviral vector resulted in a powerful growth inhibition in MCF10A cells. Based on these findings it was suggested that the amino-terminal domain may regulate the growth inhibitory activity of the internal domain. This internal domain (residues 303-1292) is lost in BRCA1a as a result of alternative splicing and it still functions as a growth suppressor. It is now seen that the growth suppressor function of BRCA1a can depend on the presence of Rb similar to BRCA1. The majority of BRCA1-related breast cancers have a typical basal epithelial phenotype, TN, grade (Tischkowitz et al., 2006, Cell Cycle 5: 963-7). There are currently no treatments that are effective against TN breast cancers. One of the challenges in breast cancer research is to discover new drugs or treatment strategies that will be effective against TN breast and hormone independent ovarian and prostate tumors. Since BRCA1a was found to be greatly reduced or absent several breast and ovarian tumors relative to BRCA1, it is seen that variation in the levels of expression of these isoforms can result in cancer.

EXAMPLE

A study in which CAL-51, and ES-2 and PC-3 cells were transfected with empty pcDNA vector or with BRCA1a, were trypsinized, washed and suspended in sterile phosphate-buffered saline solution was done to determine their tumorigenicity suspension of $1 \times 10^7$ cells in a volume of 0.2 ml of PBS were injected subcutaneously above the hind leg of four to five week old female immuno deficient nude mice (Ncr-mu). The mice were examined for tumor development every week for up to six weeks. The tumors were allowed to grow to at least 1.5-2.0 cm in diameter before sacrifice.

To determine whether BRCA1a has an effect on Cal 51/CCD160SSK tumor growth in vivo in nude mice, $1\times10^7$ Cal51/CCD160SSK-pEGFP transfectants and CAL51/CCD160SSK-EGFP-BRCA1a transfectants in the mid-log-growth phase are harvested by trypsinization and suspended in a volume of 0.2 ml of serum free culture medium. Harvested cells are injected subcutaneously above the hind leg of four to five week old female immune-deficient nude mice. The mice are then examined for tumor development every week for up to six weeks. The tumors are measured every four days with a caliper and the diameters recorded. The tumor volume is calculated by the formula: a2 b/2, where a and b are the two maximum diameters, the duration of the survival will be recorded, the mouse is euthanized and the tumor tissue collected for immunohistichemistry or western analysis as described previously Cell lines are considered to be non-tumorigenic if no tumors are seen by two to three months after injection. To monitor the expression of pEGFP-BRCA1a, in vivo images are collected using a fibered confocal fluorescent microscopy (Cell-Vizio, Discovery Technology International, Sarasota, and Fla.). This light-based in vivo imaging has been successfully used by our collaborator, Dr. Bergey, to show nanoparticle based in vivo delivery and expression of EGFP in mouse brains. Dr. Bergey and his colleagues were the first to report of the capability to non-invasively image nanoparticle mediated EGF-DNA delivery into brain cells of mice.

Inhibition of Tumorigenesis in Nude Mice by BRCA1a

| Cells Lines | mice with tumors/mice injected | | | Tumorigenicity |
|---|---|---|---|---|
| | 2 wk | 4 wk | 6 wk | |
| CAL-51 pOCDNA | 4/4 | 4/4 | 4/4 | + |
| CAL-51 BRCA1a #8 | 0/4 | 0/4 | 0/4 | − |
| ES-2 pCDNA | 6/6 | 6/6 | 6/6 | + |
| ES-2 BRCA1a | 1/6 | 1/6 | 1/6 | − |
| PC-3 pCDNA | 4/5 | 5/5 | 5/5 | + |
| PC-3 BRCA1a #4 | 1/6 | 1/6 | 1/6 | − |

Table 3 legend. CAL-51 and ES-2 and PC-3 cells transfected with empty pcDNA vector or with BRCA1a were trypsinized, washed and suspended in sterile phosphate-buffered saline solution. To determine their tumorigenicity suspension of $1 \times 10^7$ cells in a volume of 0.2 ml of PBS were injected subcutaneously above the hind leg of four to five week old female immuno deficient nude mice (Ncr-mu). The mice were examined for tumor development every week for up to six weeks. The tumors were allowed to grow to at least 1.5-2.0 cm in diameter before sacrifice.

Cell-Based Assay

This is a non-invasive fluorescence-based assay that can be used for screening agents that mimic the function of BRCA1 or activate the BRCA1 pathway in ER-positive, ER-negative, TN breast cancers and other cancers related to the BRCA1 gene. This is especially useful in cancers in younger women where BRCA1 protein is found in the cytoplasm. The subcellular localization of RFP-epitope tagged BRCA1a, BRCA1a Mutant No. 1 and BRCA1a mutant No. 4 after transfection into normal human MCF 10A cells was studied using live image analysis. Exclusive cytoplasmic localization of both Mutant No. 1 and Mutant #4 was observed, unlike BRCA1a, which was both in the nucleus and in the cytoplasm. Similar results were obtained using ER-positive MCF-7 and TNBC cells obtained from African American women. These mutants do not bind to Ubc9, do not suppress tumor growth, are impaired in their SUMO and Ubc-9-dependent E3 ubiquitin ligase activity and localize in the cytoplasm. This non-invasive fluorescence-based assay is simple and rapid for screening agents that can modulate the relocation of cytoplasmic RFP-tagged BRCA1 Mutants Nos. 1 and 4 proteins to the nucleus. The method could be used in evaluating potential agents for treatment of these treatment-resistant tumors and for evaluating newly-discovered mutants.

Methodology

MCF 10A or HCC-70 cells ($2\times10^5$) were seeded into the 6-well plates the day before transfection. The following day, Red Fluorescent Protein (RFP)-taged BRCA1a or its mutants (2 μg) were transected into the cells using Lipofactamine 2000 transfection agent (Invitrogen). The nuclei were visualized with DNA staining dye Hoechst (Invitrogen) after 24 hours of transfection. MCF 10A and HCC-70 live images were taken with Olympus fluorescent microscope (20×)

Figure 2:
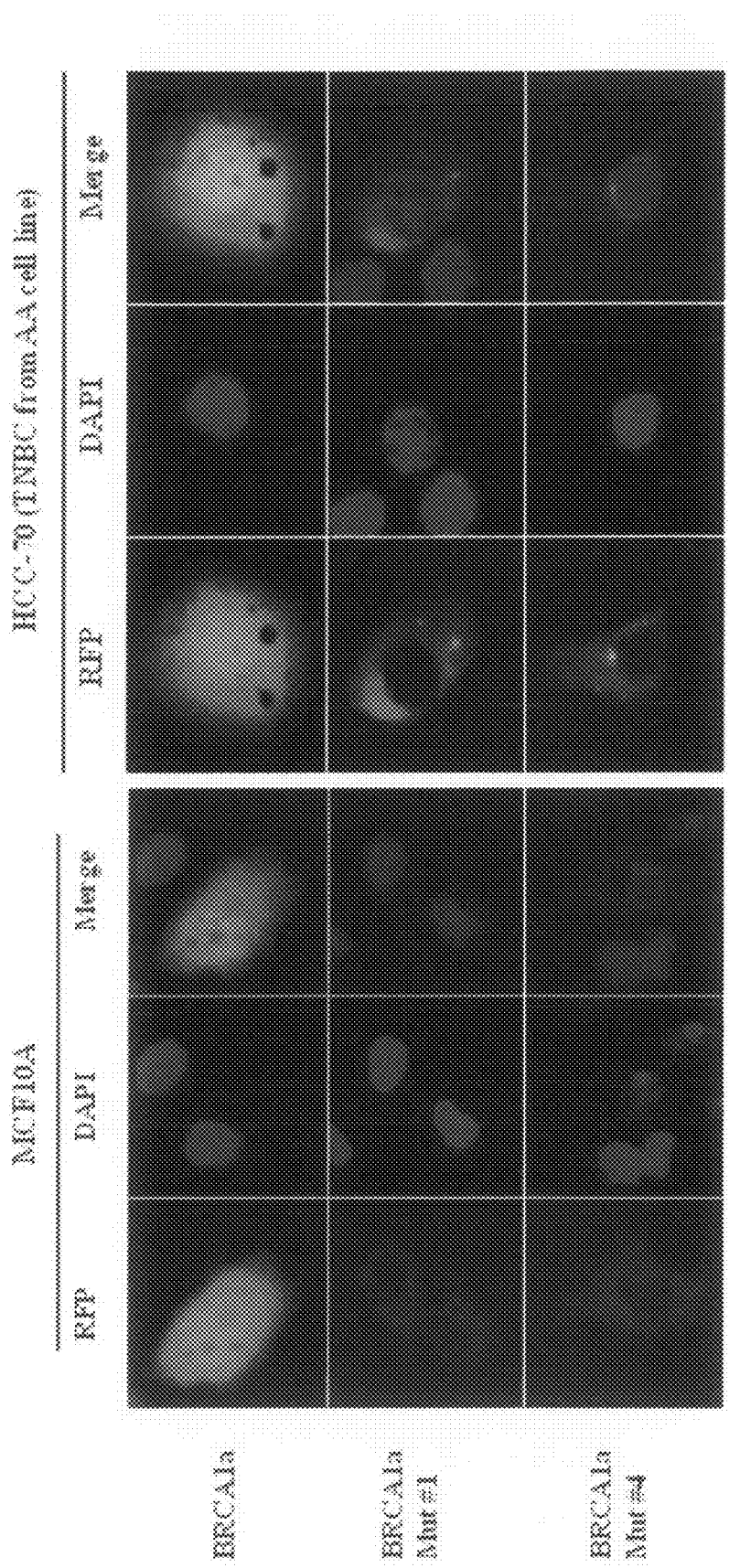
FIG. 2: Shows methodology for cell-based assay 4.

FIG. 2 shows both RFP BRCA1a Mutants 1 and 4 are localized in the cytoplasm of MCF10A and HCC-70 cells, unlike RFP BRCA1a, using live image. DNA was stained with DAPI.

Many patients who do have breast cancer, especially among African American and Hispanic populations, do not have genes that appear mutated but do, however, have TN malignancies. It has now been found that malignancies can result from errors in posttranslational modification of proteins. The methods of the invention respond to posttranslational modifications of proteins which would not be identified using cDNA probes. The use of the methods of the invention identifies those instances when the DNA can appear normal but the posttranslational modification errors gives rise to the disease condition. Furthermore, the methods of the invention, especially the fluorescence-based assay, provide means for testing agents that may be useful for the particular patient.

Finally, the methods of the invention can be used to determine whether a particular environmental agent has a detrimental effect on patients with these kinds of malignancies. For example, the assay using luciferase activity provides a means of evaluating the function of BRCA1 or mutant BRCA1 by evaluating luciferase activity wherein increased or decreased activity depending on the assay used is evidence of desirable (non-tumorogenic) function. The addition of a putative toxin or therapeutic agent would give evidence of effect on luciferase activity whether increase (therapeutic indication) or decrease (toxic effect).

Considering a cell-based method, the evidence of cytoplasmic deposition of the fluorogen-tagged BRCA1 component would indicate a deleterious result. The addition of a putative therapeutic agent would be evaluated for deposit of the tagged BRCA1 component in the nucleus. Alternatively, increased deposition of the fluorogen-tagged BRCA1 protein in the cytoplasm could be deemed evidence of toxic effect.

What is claimed is:

1. A method of screening small molecules that complement a breast cancer susceptibility gene 1 (BRCA1) defect comprising the steps of:
    a) coexpressing Ubc9, SUMO-1, estrogen receptor (ER) α and a reporter in isolated cells comprising a reporter gene under the control of an estrogen responsive element (ERE), wherein the reporter gene is a luciferase gene;
    b) inducing the cells with estrogen (E2) after transfection;
    c) treating the cells with a small molecule compound;
    d) harvesting the cell after sufficient time to allow luciferase expression; and
    e) measuring luciferase activity from said cells;
    wherein an increase in luciferase activity in treated cells as compared to non-treated cells indicates that the small molecule is capable of complementing a BRCA1 defect; and
    wherein a decrease or no effect in luciferase activity in treated cells as compared to non-treated cells indicates that the small molecule is not capable of complementing a BRCA1 defect.

2. The method of claim 1, wherein the cells are Triple-Negative (TN) breast cancer cells.

* * * * *